(12) United States Patent
Oyster et al.

(10) Patent No.: US 8,485,429 B2
(45) Date of Patent: Jul. 16, 2013

(54) METHOD AND APPARATUS FOR LABELING GOODS

(75) Inventors: Bradley S. Oyster, South Lyon, MI (US); Edward M. Weber, Northville, MI (US)

(73) Assignee: Toolworx Information Products, Inc., Brighton, MI (US)

( * ) Notice: Subject to any disclaimer, the term of this patent is extended or adjusted under 35 U.S.C. 154(b) by 137 days.

(21) Appl. No.: 13/091,262

(22) Filed: Apr. 21, 2011

(65) Prior Publication Data

US 2012/0267428 A1    Oct. 25, 2012

(51) Int. Cl.
*G06K 5/00* (2006.01)
*G06F 17/00* (2006.01)

(52) U.S. Cl.
USPC ............................................ 235/375; 235/380

(58) Field of Classification Search
USPC ................. 235/375, 380, 382, 492, 486, 487
See application file for complete search history.

(56) References Cited

U.S. PATENT DOCUMENTS

| | | | | |
|---|---|---|---|---|
| 6,111,639 | A * | 8/2000 | Reduto | 356/300 |
| 6,535,637 | B1 * | 3/2003 | Wootton et al. | 382/190 |
| 2010/0324936 | A1 * | 12/2010 | Vishnubhatla et al. | 705/3 |

* cited by examiner

*Primary Examiner* — Thien M Le
(74) *Attorney, Agent, or Firm* — Brooks Kushman P.C.

(57) ABSTRACT

A computer-implemented method includes receiving a container image including container content characteristic information. The illustrative method further includes analyzing the container content characteristic information and determining the identity of the container contents based on the container characteristic information. Also, the method includes transmitting container content identity information for printing a bar code relating to the container content identity information. The method additionally includes generating a bar code based on the container content identity information. The illustrative method also includes printing a label including the bar code relating to at least the container content identity information.

16 Claims, 9 Drawing Sheets

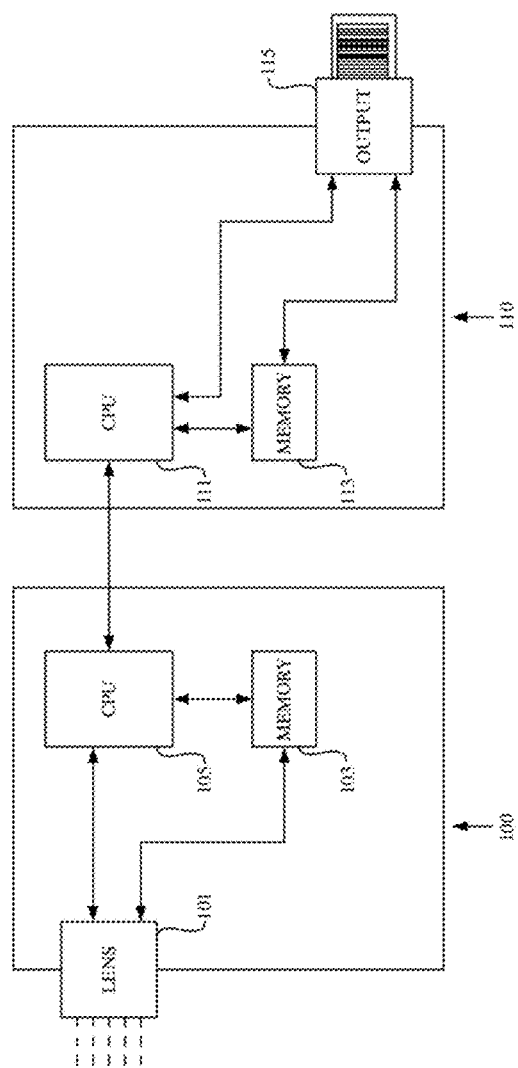

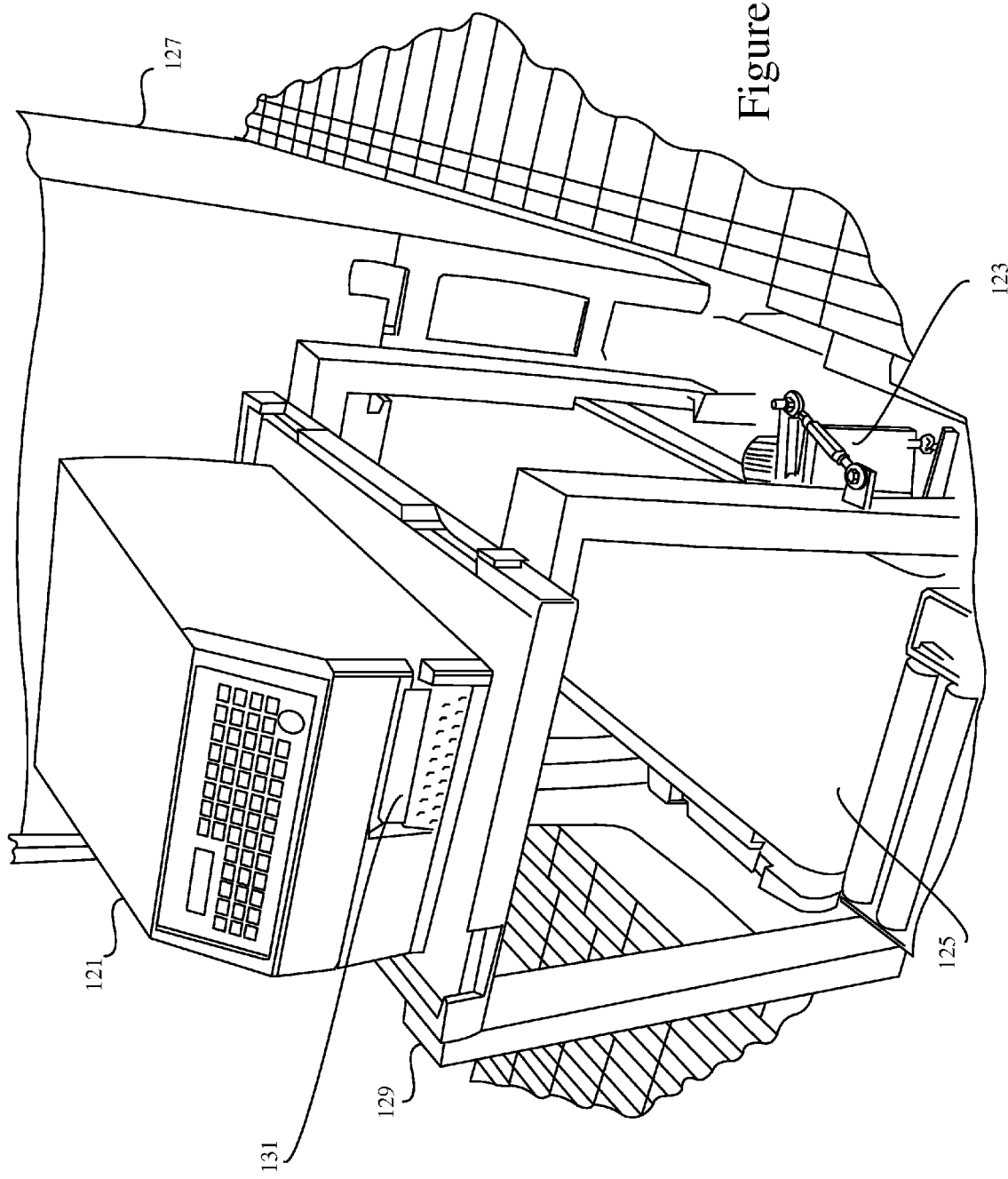

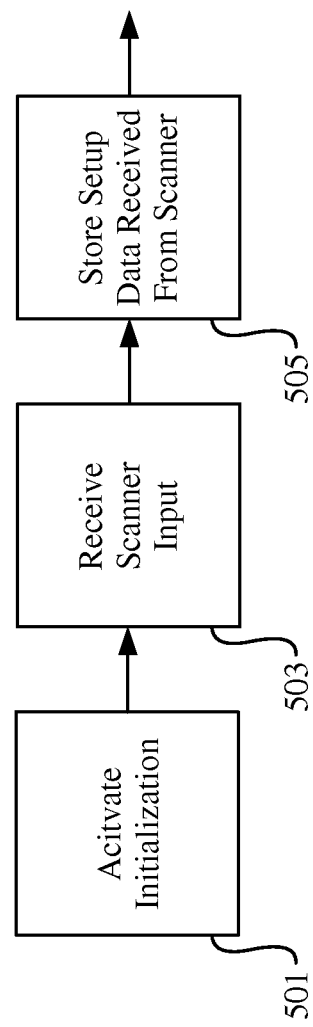

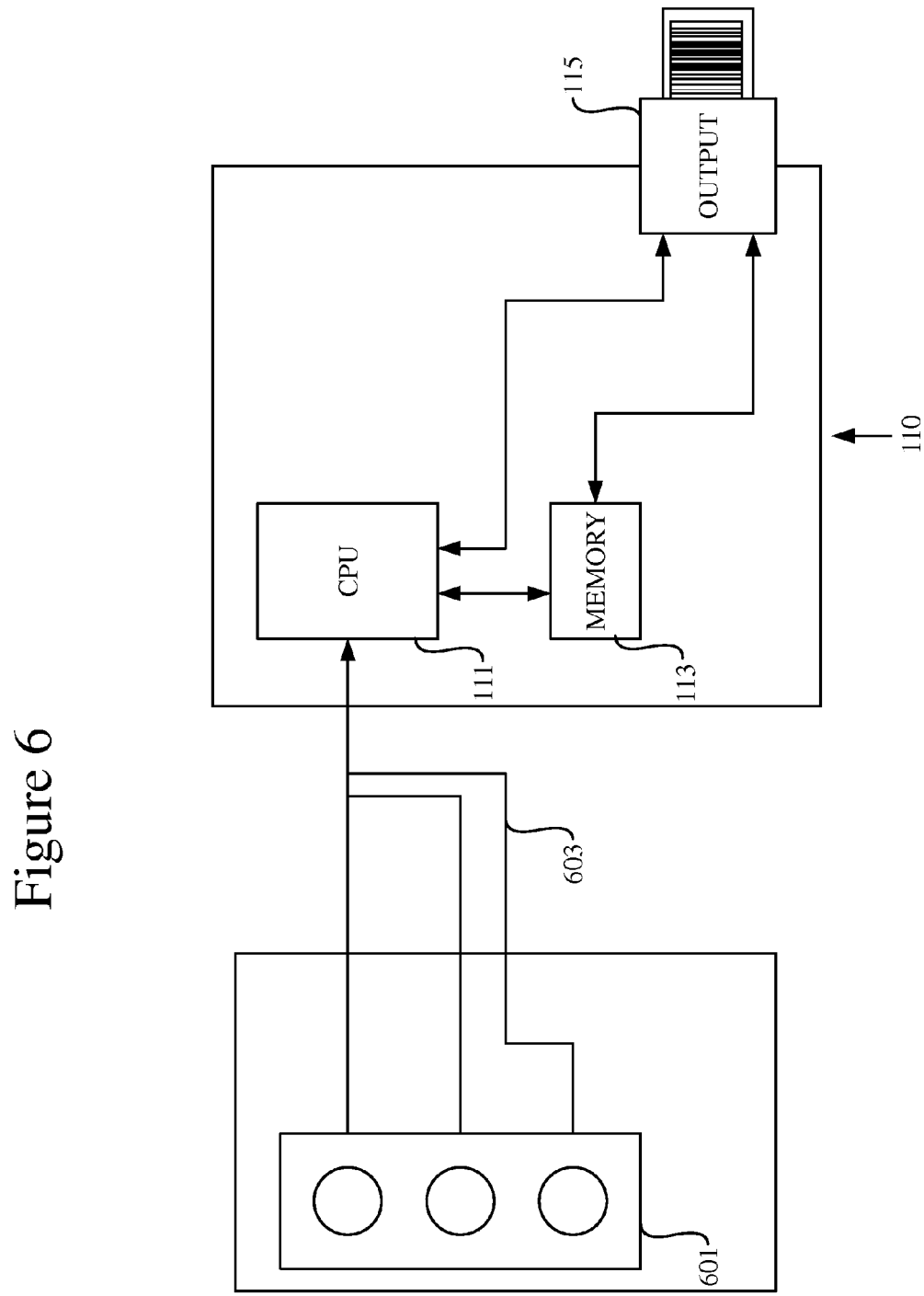

METHOD AND APPARATUS FOR LABELING GOODS

TECHNICAL FIELD

The illustrative embodiments generally relate to a method and apparatus for labeling goods.

BACKGROUND

Modern harvesting is a synergy of manpower and machine power. As human harvesters move through fields gathering vegetables, they work in conjunction with massive packing machines that allow for rapid collection and processing of boxes of produce. Workers load the harvest into individual boxes, according to a particular plan for that product, and then the boxes are loaded onto the packing machine.

In at least one example, the packing machine is equipped with a conveyor belt that conveys the boxes to a common location for stacking and/or labeling. In existing systems, a grid on the boxes may be marked with, for example, a grease pen. The mark in the gird can denote which type of produce is in the box (and possibly how much of the produce), based on, for example, row and column correspondence. Once the box has been marked and packed with goods, it can be stacked for later processing at a warehouse.

SUMMARY

In a first illustrative embodiment, a computer-implemented method includes receiving, via a vision system, a container image including container content characteristic information. The illustrative method further includes analyzing, via a vision system, the container content characteristic information and determining the identity of the container contents based on the container characteristic information.

Also, in this embodiment, the method includes transmitting container content identity information for printing a bar code relating to the container content identity information. The method additionally includes generating a bar code based on the container content identity information.

The illustrative method also includes printing a label including the bar code relating to at least the container content identity information.

In a second illustrative embodiment, an apparatus includes a camera, operable to obtain an image of at least a portion of a container in motion along a belt and to determine information relating to contents of the container from the image. The illustrative apparatus also includes a printer, operable to print at least a bar code label, and in direct communication with the camera.

In this embodiment, the camera is further operable to relay the determined information relating to the contents of the container to the printer. Also, in this embodiment, the printer is operable to process the information relayed from the camera to generate a bar code relating to the contents of the container. According to this embodiment, the printer is operable to print the generated bar code relating to the contents of the container.

In a third illustrative embodiment, a processing system includes a field packaging vehicle, operable to receive boxes on a conveyor system included therewith, and convey the boxes along the belt. The illustrative system also includes a vision system camera, operable to view at least a marked portion of the boxes as the boxes are conveyed along the belt. The illustrative system further includes a printer, operable to print bar code labels and in communication with the camera.

In this exemplary system, the conveyor system is operable to convey received boxes past a viewing lens of the vision system camera. Also, in this system, the vision system camera is operable to determine information relating to the contents of the boxes from the marked portion and to convey the information directly to the printer. According to this illustrative system, the printer is operable to encode information relating to the contents of the box into a label printable by the printer for application to the box.

BRIEF DESCRIPTION OF THE DRAWINGS

The examples and figures shown herein are provided for illustrative purposes only, and are not intended to limit the scope of the invention. Further understanding of illustrative embodiments can be gained by referral to the Figures, in which:

FIG. 1A shows an exemplary schematic of a vision system operable to produce barcodes for product labeling;

FIG. 1B shows an exemplary vision system working in conjunction with a packing machine;

FIG. 5 shows an illustrative example of an initialization process; and

FIG. 6 shows one example of an alternative input device.

DETAILED DESCRIPTION

Figure 2:
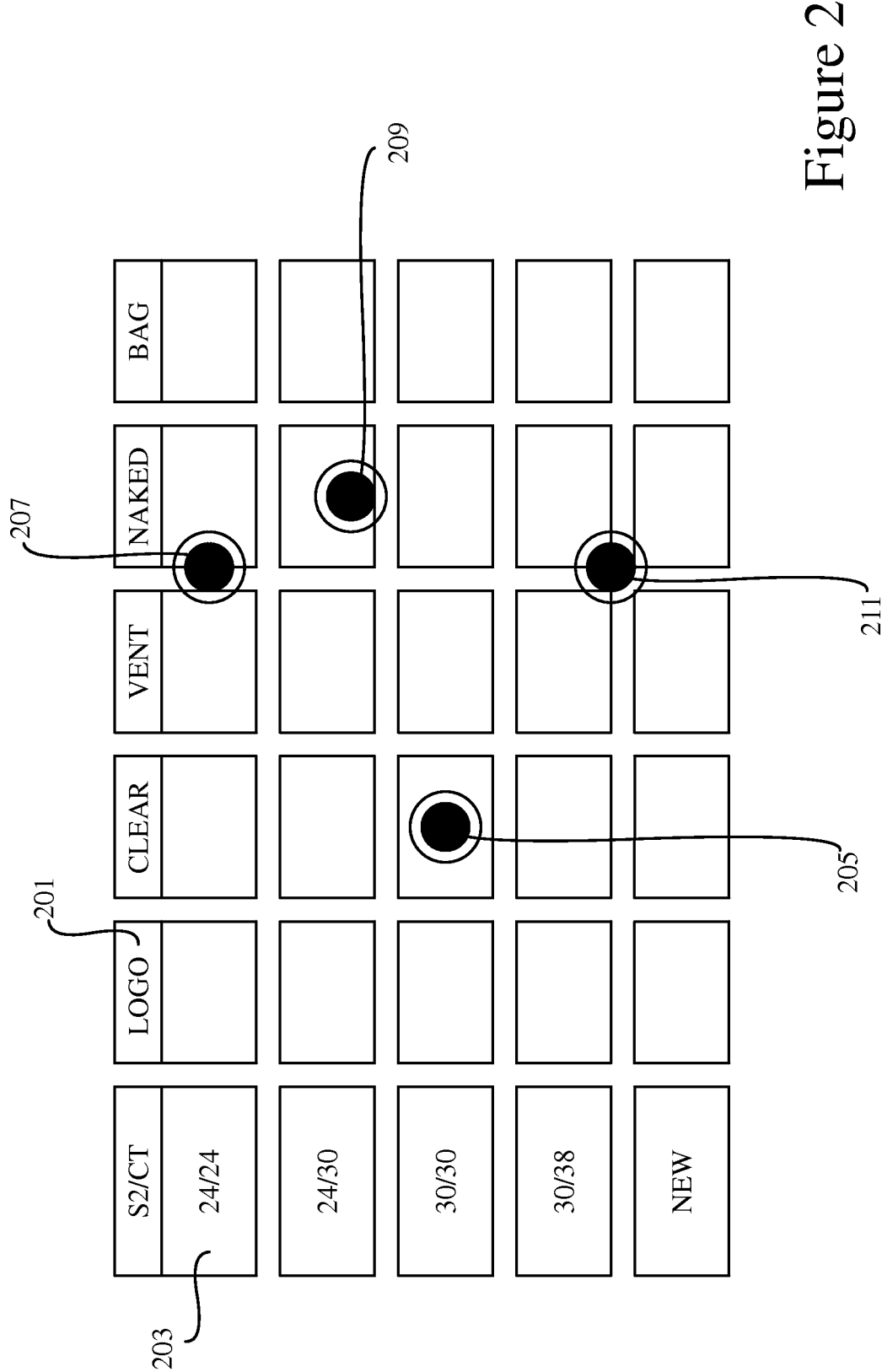
FIG. 2 shows an illustrative example of a marking designation for a box.

The illustrative examples presented herein are shown for purposes of example only, and are not intended to limit the scope of the invention thereto. Alternatives to steps and/or elements of the processes and apparatuses hereby disclosed are contemplated to also be within the scope of the invention.

The illustrative embodiments present a vision system operable to work in conjunction with a packing machine or harvester operating in the field. Through application of the illustrative embodiment, products can be swiftly and accurately labeled with barcodes in the field. By barcoding the products, faster and more accurate processing later in the production process may be possible.

In a first illustrative embodiment, shown in FIG. 1A, a camera 100 works in conjunction with a label printer 110. Although shown as separate entities, it may be possible to combine the camera and laser printer into a single device and still accomplish the illustrative methods described herein. In this illustrative example, a COGNEX vision camera is used, although any suitable camera outfitted with the capability to communicate with a label output device may be used. Additionally, in this embodiment, also as an illustrative example, an INTERMEC barcode label printer is used in conjunction with the camera. Again, any label printer with capability of interacting with a vision system may be used.

Deployment of the camera and printer in one illustrative example is shown in more detail in FIG. 1B. As can be seen in FIG. 1B, the camera may be deployed so that it is capable of viewing boxes that move down a conveyor. As the camera images the box, it sends a signal to the printer and a label corresponding to the markings indicating box contents may be printed for application to the box.

In one illustrative embodiment, the vision system camera is suitable for deployment in a working field environment. It may be equipped with a lens 107, capable of imaging a box, for example, as the box moves along a conveyor belt. The image may be conveyed from the lens to a memory 103 and/or an internal CPU 105 within the camera. If the camera is equipped with both a memory and a CPU, the memory and CPU may also be capable of bi-directional communication. In this illustrative embodiment, processing of the image taken by the camera is split between the printer and the camera, but this is shown for illustrative purposes only.

Although this example shows an instance where the camera does a first processing step and the printer does a second processing step, it would also be possible to perform the processing steps within the printer or within the camera, and it would further be possible to combine the two devices into a single device capable of performing the processing steps detailed herein.

In addition to the vision systems camera 100, this illustrative system includes a label printer 110. In this example, the printer is capable of printing barcode labels at a high enough speed that they can be removed and applied to boxes that move along a conveyor belt, although any printer suitable for the task at hand and capable of meeting operator needs may be used.

The printer in this example is also equipped with a CPU 111 in communication with a memory 113 and an output 115. The output may further be in communication with the memory 113. In this example, the output 115 refers to the print head (or other printing mechanism) that outputs the printed labels under instructions from the processor.

Working in conjunction, the camera and printer can operate to smoothly and efficiently read markings on boxes in the field and produce labels in a rapid and suitable manner so that the boxes can be labeled with the labels for later processing. One illustrative example of the system in application is shown with respect to FIG. 1B.

In the illustrative example shown in FIG. 1B, a printer 121 is seated on a platform 129 over a conveyor belt 125. In this illustrative example, the conveyor belt is provided as part of a packaging apparatus that travels in the field with harvesting workers. As boxes of produce are picked and filled, they are loaded on to the conveyor belt. They pass down the belt and through the portion 127.

As the boxes leave the portion preceding the platform, the camera 123 can see the forward facing portion of the box. The camera is mounted such that it can see the exit of the portion 127, and can capture an image of the box as it leaves that portion. The camera is in communication with the printer 121, and is operable to relay information about the box image to the printer.

Once the box image has been processed, either by the camera, the printer, or by a combination of both, a label 131 is printed. The label can then be applied to the box as it rolls beneath the printer, allowing efficient labeling of the box with a pre-printed label corresponding to the contents of the box. Since the printer can dynamically adapt to markings on the box indicating contents, the packaging machine may be able to work its way through different types of crops and different packing of boxes without having to retool or reconfigure the printer/camera.

FIG. 2 shows an illustrative example of a marking designation for a box. This marking 200 comes in the form of a grid in this illustrative embodiment. The grid may be pre-printed on to the boxes, and columns in the grid 201 may represent a produce type, and rows in the grid 203 may represent a produce quantity. Any other suitable designations may be assigned to the rows and columns, with points where rows and columns meet designating a particular combination of item and quantity.

The grid may be easily marked with a dot 205. In this illustrative example, the dot 205 is a sticker that can be placed in the appropriate location, and that is detectable by the vision system. Any suitable means of marking the packaging can be used, provided that the marking can be detected by the vision system.

Since the dots are applied by hand, in this example, there may be overlap between rows and columns, due to misplacement of dots. Dot 207 is a dot that has been overlapped between two columns. Dot 209 is a dot that has been overlapped between two rows, and dot 211 is a dot that has been overlapped between both columns and rows.

Although the dots 207, 209 and 211 are not squarely within a row column designation, the processing software that analyzes the image of the grid may be operable to determine which is the most likely column and/or row to which the dot or other marking applies. In this manner, even if a marking is misplaced, the system should be able to continue to function.

Figure 3A:
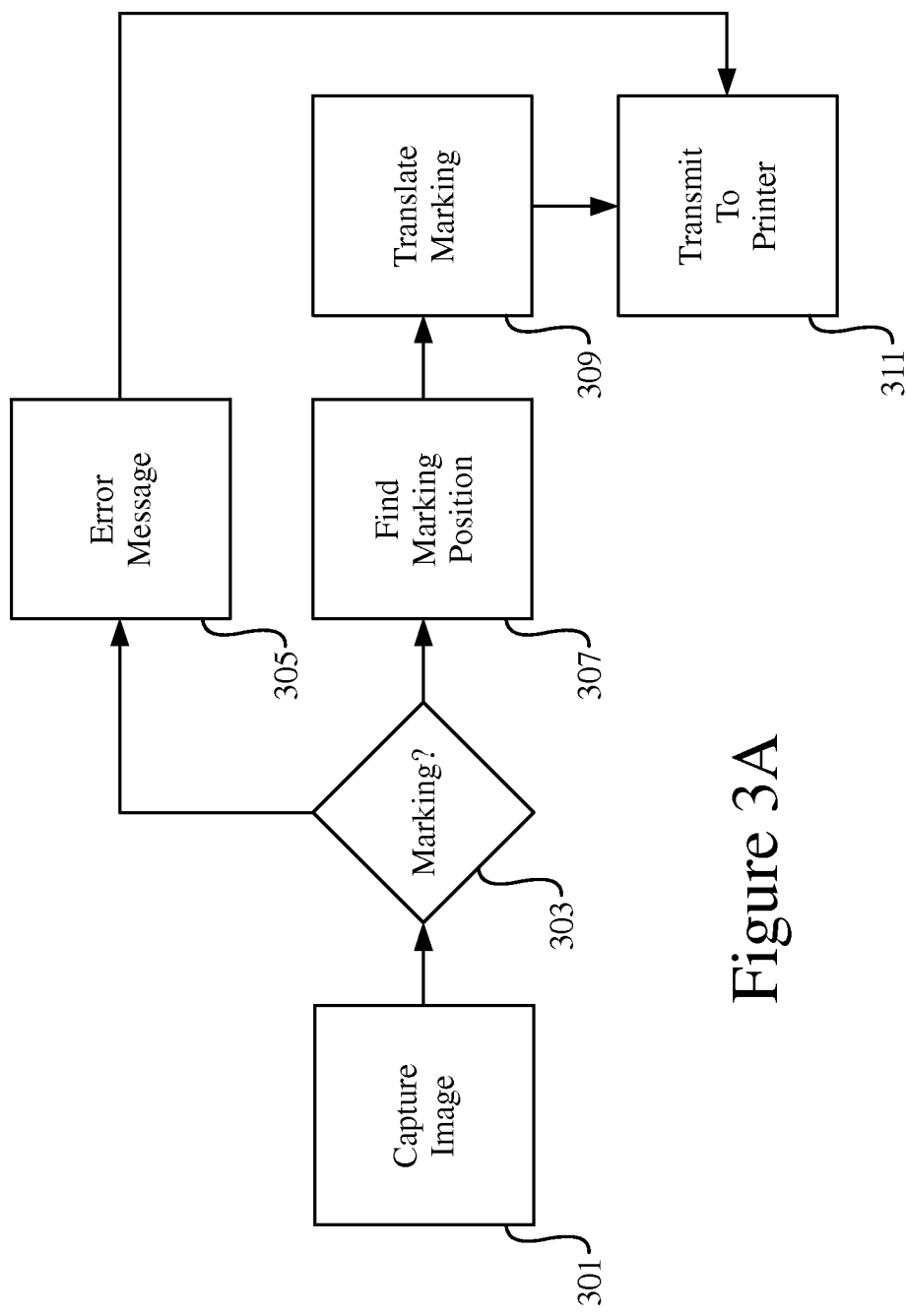
FIG. 3A shows an illustrative example of a process for imaging a box marking.

FIG. 3A shows an illustrative example of a process for imaging a box marking. In this illustrative example, the process is run within the camera, but the process could also be run within a printer in communication with the camera. In this illustrative process, the camera first images the grid on the box as it passes through the viewing field of the camera 301. Other suitable designators on the box could also be imaged.

Once the image is obtained, the process next checks to see if there is a marking that corresponds to box contents 303. In this particular example, the marking is a dot on a grid designating a produce type and a number of produce, but any suitable designation can be used depending, for example, on box contents and working environment.

If there is no marking, or, in this example, if the marking is indistinguishable or the designation cannot be determined (if, for example, the marking is not clearly in a particular row or column), then the process may generate an error message 305. Otherwise, if there is an understandable designation of box contents, the process determines which position on the grid is occupied by the marking 307. Once a grid position has been determined, the process may translate that marking into a form that is understandable by the printer 309.

In another illustrative embodiment, the grid position (without the translation) may be transferred to the printer.

In this illustrative embodiment, the translated grid coordinates are transferred to the printer 311. If an error message was generated, due, for example, to a marking problem, then that information may be transferred to the printer additionally or alternatively 311.

Figure 3B:
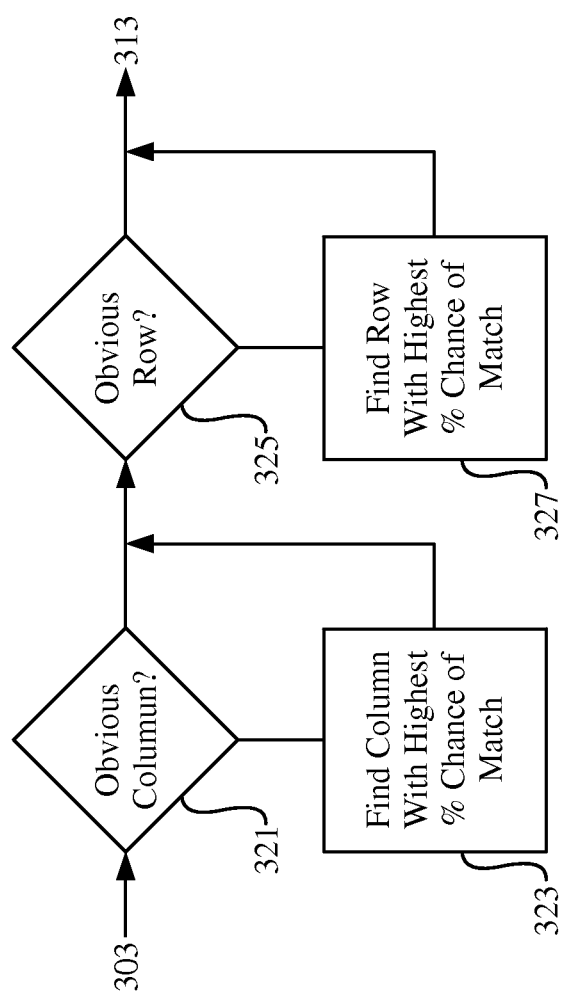
FIG. 3B shows an illustrative example of a process for interpreting a grid position of a mark.

FIG. 3B shows an illustrative example of a process for interpreting a grid position of a mark. This is just one example of how the process shown in 3B may interpret an image of a grid viewed on a box. In this illustrative example, once it has been determined that there is a marking on the grid 303, the process checks to see if there is a clear column to which the marking corresponds 321. If there is no clear column, the process may engage in some additional logic to determine a likely candidate 323, such as, but not limited to, selecting a column with the highest portion of the dot therein.

Once the process has been completed for the column, it is then repeated for determining the row in which the dot lies. In this embodiment, the process checks to see if there is a clear row in which the marking lies 325. If the row is unclear, the process may again employ some logic for determining which row is likely the designated row 327.

The process described above is merely an exemplary process for determining a marking position and any suitable replacement is also within the scope of the invention.

Figure 4A:
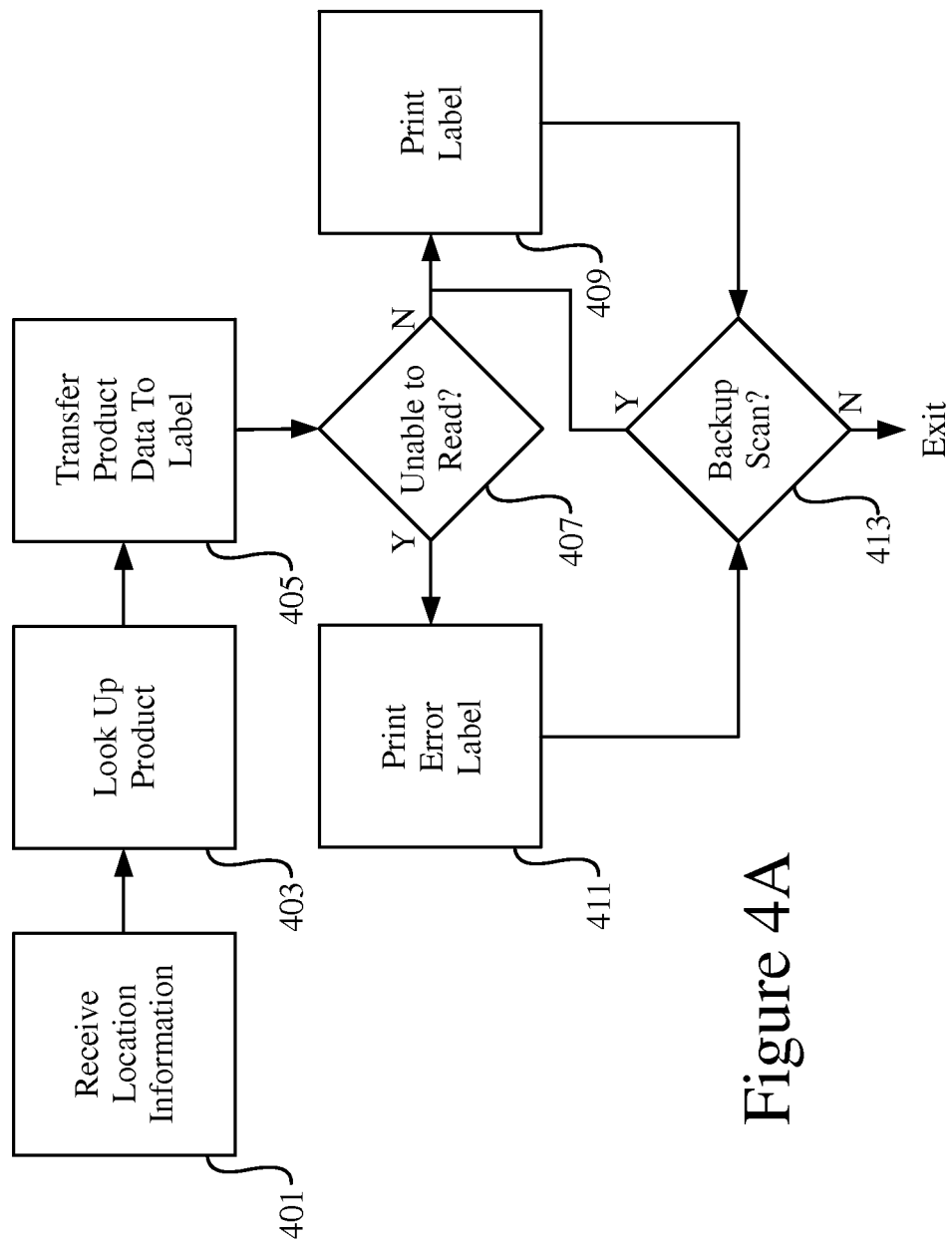
FIG. 4A shows an illustrative example of analyzing a box marking image and preparing a label.

FIG. 4A shows an illustrative example of analyzing a box marking image and preparing a label. In this illustrative example, the process is performed by the printer, having received data from a camera. In another example, the camera could perform the process of FIG. 4A, or a similar process could be performed by the printer or the camera to produce the results described herein.

In this illustrative embodiment, the process receives a marking location from the camera 401. In this embodiment the location is in the form of a matrix location, but any suitable format would be acceptable. The matrix location is a location that designates the marking that was read from the box. The matrix location received from the camera, in this embodiment, is cross-referenced with a look-up table to determine the characteristics of the product in the box 403. Although a matrix location is used here and cross referenced with a look-up table, any suitable manner of processing a marking to determine box contents could be used. Once the product has been determined from a lookup, a database, a data repository access, etc., the information relating to the product can be converted into a bar-code format and transferred to a label 405.

In this illustrative example, if there was an error reading the marking on the box, a "no read" signal may have been present 407. Other suitable error condition signals may also be used, including a plurality of signals designating different errors depending on an actual error that occurred.

In this embodiment, if a "no read" or other error signal has been detected, an error label is printed 411 so that the operator knows that an error has occurred. In another example, the printer or camera or other suitable device may indicate in another manner to the operator that a visual read of the box marking was unsuccessful (or any other suitable error designation corresponding to an occurring error).

If there was no error, then, in this illustrative example, the printer prints a label 409 and the label can be affixed to the box. In this embodiment, after printing an error code and/or after printing a label, the machine may wait briefly to determine if the operator wishes to manually scan an entry (to produce a replacement label, for example). In one illustrative instance, an unreadable box may have come through the machine, and the operator, after receiving an error message, may wish to manually input label data so that the box can be labeled.

In one illustrative example, the manual input of label data can be done through a quick scan of a bar-code corresponding to a label to be printed. The bar-code is then used to generate the label, and the label can be printed and applied to the box. Even when a label prints, this technique may be used, because it is possible that an improper label could have printed.

If there is no backup scan to be done 413, the process exits and moves on to the next box to be processed.

Figure 4B:
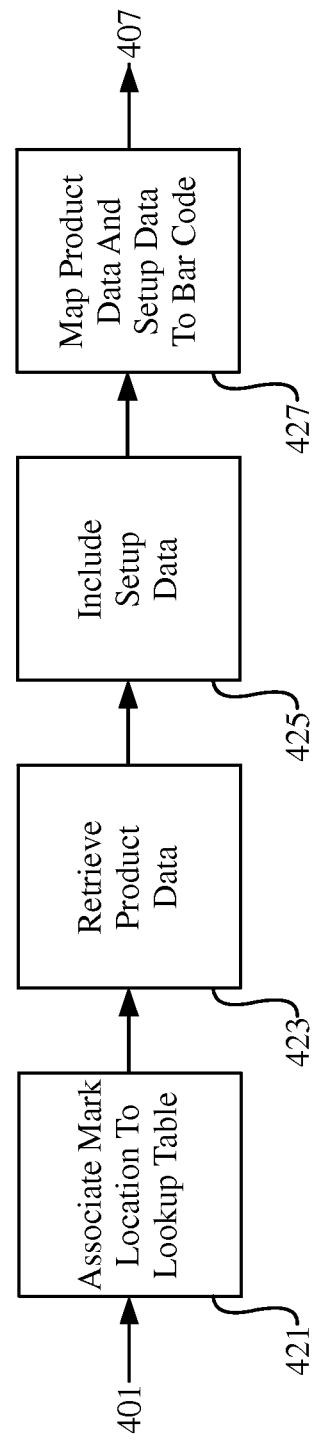
FIG. 4B shows a further illustrative example of preparing a label.

FIG. 4B shows a further illustrative example of preparing a label. In this illustrative example, the printer has received data from the camera in the form of a matrix. Again, in this example, the matrix was derived from the image the camera took of the markings and grid on a box passing in front of the camera.

One the matrix has been received 401, the process associates a location in the matrix with an association in a lookup table 421. This is one illustrative example of data retrieval, any known suitable method will suffice. Once the entry in the lookup table has been determined, the illustrative process retrieves data relating to the boxed product from the entry 423. This data may be used to produce a label that can be used to label the boxed product.

Once the data has been retrieved from the entry, there may also be additional data to consider 425. In this embodiment, the operator may have input some base information to be affiliated with all the boxes or a run of boxes. In another embodiment, there may be some preprogrammed information that also needs to be included with the labels to be placed on the boxes.

This illustrative process retrieves the setup or common data, and maps the lookup table data and the setup data to a bar code format 427. The mapping to the bar code format can be done using known techniques for translating data to a bar code. Once all the relevant data has been mapped to a bar code format, the label can be printed for application to the product box.

FIG. 5 shows an illustrative example of an initialization process. In this illustrative example, an operator desires to input data into the printer for processing in conjunction with the box scans. The printer may have, for example, a bar code scanner or other input device attached thereto. In this embodiment, the printer begins an initialization procedure 501. This procedure may expect some input from a user after activation.

In this example, the printer waits until a signal from the attached bar code scanner is received 503. The scanner input may come from a reading of an external bar code, for example, that allows the operator to easily input data for use by the printer. Once the data has been received, the printer stores the data as setup data 505 to be used with the next batch of boxes to be processed, for example.

FIG. 6 shows one example of an alternative input device. In addition to receiving input from a vision systems camera, the printer may receive input from alternative devices. These devices may include, but are not limited to, hand scanners, button input devices, etc.

One illustrative example of a button input device is shown with respect to FIG. 6. In this illustrative embodiment, the device includes a plurality of buttons that are pre-programmed to correspond to varying types of product.

For example, in one illustrative embodiment, a device operator may program the buttons 601 at the onset of operations. When a particular product comes down a conveyor belt, in one embodiment, the operator may select a button 601 corresponding to that product.

Selection of a button, in this embodiment, causes activation of an electric signal 603 corresponding to the particular button. The signal is received by the printer, and, based on the particular signal that was activated, the printer knows the product for which to print a label. Appropriate label data is then aggregated by the printer, if necessary, and a label corresponding to the product is produced.

In one embodiment, each button corresponds to a particular electric line between an input button box and the printer. Activation of a particular button causes activation of a particular line. Accordingly, the box itself, in this embodiment, merely provides the signal to the printer, which the printer then interprets based on previously defined input.

Alternatively, the box may have more complex electronics associated therewith, and in another embodiment, the identification of the product may be done in the button input box and corresponding identification may be transmitted to the printer.

As with the printer shown in FIG. 1, the printer in this illustrative embodiment may have a processor 111 associated therewith. The printer may also have a memory 113, which may include at least information about the particular signals to be received from the input box. Further, the printer may be capable of printing a bar-code label having relevant product information encoded thereon.

Although the invention is described in terms of illustrative embodiments, these are provided as examples only and are not intended to limit the scope of the invention in any manner.

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A computer-implemented method comprising:
    receiving, via a vision system, a container image including container content characteristic information;
    analyzing, via a vision system, the container content characteristic information;
    determining container content identity information based on the container characteristic information;
    transmitting the container content identity information for printing a bar code relating to the container content identity information;
    generating a bar code based on the container content identity information; and
    printing a label including the bar code relating to at least the container content identity information.

2. The method of claim 1, wherein the container content characteristic information includes a grid having two or more rows and two or more columns.

3. The method of claim 2, wherein the container content characteristic information further includes at least one marking on the grid designating at least one of the rows and at least one of the columns.

4. The method of claim 3, wherein the marking is a dot.

5. The method of claim 1, wherein the generating step includes retrieving information, for inclusion in the bar code, relating to the container contents from a data repository.

6. The method of claim 5, wherein the data repository is a database.

7. The method of claim 6, wherein the data repository is a look-up table.

8. The method of claim 5, further comprising:
    combining information resulting from the retrieving step with additional product information to generate a bar code including both information resulting from the retrieving and the additional product information.

9. An apparatus comprising:
    a camera, operable to obtain an image of at least a portion of a container in motion along a belt and to determine, based on visual information provided on a container's surface, visible in the image of at least the portion of the container, information relating to contents of the container;
    a printer, operable to print at least a bar code label, and in direct communication with the camera;
    wherein, the camera is further operable to relay the determined information relating to the contents of the container to the printer and wherein the printer is further operable to process the information relayed from the camera to generate a bar code relating to the contents of the container, and wherein the printer is operable to print the generated bar code relating to the contents of the container.

10. The apparatus of claim 9, wherein the camera is operable to recognize a grid included in the obtained image.

11. The apparatus of claim 10, wherein the camera is operable to recognize a marking on the grid included in the obtained image.

12. The apparatus of claim 11, wherein the camera is operable to translate the recognized marking to a matrix for relay to the printer.

13. A processing system comprising:
    a field packaging vehicle, operable to receive boxes on a conveyor system included therewith, and convey the boxes along the belt;
    a vision system camera, operable to view at least a marked portion of the boxes as the boxes are conveyed along the belt; and
    a printer, operable to print bar code labels and in communication with the camera;
    wherein the conveyor system is operable to convey received boxes past a viewing lens of the vision system camera, and wherein the vision system camera is operable to determine information relating to the contents of the boxes from the marked portion and to convey the information directly to the printer, and wherein, the printer is operable to encode information relating to the contents of the box into a label printable by the printer for application to the box.

14. The system of claim 13, wherein the marked portion of the boxes are marked with a grid.

15. The system of claim 14, wherein a marking within the grid denotes box contents.

16. The system of claim 13, wherein the information about the viewed marking includes information describing box contents.

* * * * *